United States Patent [19]

Hashizume et al.

[11] Patent Number: 4,618,613
[45] Date of Patent: Oct. 21, 1986

[54] PREVENTIVE AND HEALING COMPOSITION FOR DISEASES DUE TO LIPOXYGENASE METABOLIC PRODUCTS

[75] Inventors: Kazuko Hashizume, Tokyo; Hiroshi Kase, Koganei; Shigeto Kitamura, Machida; Takao Iida, Hofu; Kunikatsu Shirahata, Komae; Kenji Omori, Mishima; Katsuichi Shuto, Shizuoka, all of Japan

[73] Assignee: Kyowa Hakko Kogyo Company, Ltd., Tokyo, Japan

[21] Appl. No.: 749,716

[22] Filed: Jun. 28, 1985

Related U.S. Application Data

[63] Continuation of Ser. No. 606,997, May 3, 1984, abandoned.

[30] Foreign Application Priority Data

May 12, 1983 [JP] Japan ................................. 58-83339

[51] Int. Cl.⁴ ............................................. A61K 31/47
[52] U.S. Cl. .................................... 514/312; 514/826
[58] Field of Search ................................ 514/312, 826

[56] References Cited

PUBLICATIONS

Lightbrown et al, Biochem. J. (London), vol. 63, 130-7 (1956).

*Primary Examiner*—Leonard Schenkman
*Attorney, Agent, or Firm*—Antonelli, Terry & Wands

[57] ABSTRACT

A preventive and healing composition for diseases due to lipoxygenase metabolic products, which comprises an effective amount of a compound represented by the formula:

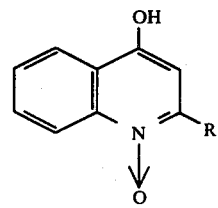

wherein R is an alkyl group having 1 to 15 carbon atoms and at least one pharmaceutically acceptable carrier.

9 Claims, 1 Drawing Figure

PREVENTIVE AND HEALING COMPOSITION FOR DISEASES DUE TO LIPOXYGENASE METABOLIC PRODUCTS

This is a continuation of application Ser. No. 606,997, filed May 3, 1984, now abandoned.

This invention relates to a preventive and healing composition for diseases due to a lipoxygenase inhibition. More particularly, the present invention relates to a preventive and healing composition for diseases due to lipoxygenase metabolic products, which comprises an effective amount of a compound represented by the formula:

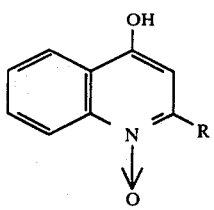

wherein R is an alkyl group having 1–15 carbon atoms and at least one pharmaceutically acceptable carrier.

Lipoxygenase (1. 13. 11. 12) is an enzyme existing in blood platelets, leukocytes, lymphocytes, etc., and is an enzyme which converts polyvalent unsaturated fatty acid (particularly arachidonic acid) to hydroperoxy acid. It is known that positions of hydroperoxy group(s) introduced in arachidonic acid by lipoxygenase are 5th, 8th, 9th, 11th, 12th and 15th positions. For example, it has been reported that lipoxygenase existing mostly in blood platelets, etc., is an enzyme that hydroperoxidizes the 12th position of arachidonic acid (12-lipoxygenase), and there are 5-lipoxygenase and 15-lipoxygenase in leukocytes. Hydroperoxyeicosatetraenoic acid formed from arachidonic acid by lipoxygenase is unstable and is converted to hydroxyeicosatetraenoic acid. These fatty acids formed by lipoxygenase stimulate by themselves physiological actions such as migration of leukocytes and smooth muscles of aortic tunica media, etc., and it has been recently clarified that they are further metabolized, in vivo, to produce metabolic products having various physiological actions. For example, chemical structure and biosynthesis route of a slow reacting substance of anaphylaxis (abbreviated as SRS-A, which includes leukotriene C, D, E and F) which is formed in lungs of guinea pigs at anaphylaxis or human lungs at asthmatic attacks and has a force to slowly but strongly contract the smooth muscles of bronchus and which has long been regarded as a substance to cause asthma have been recently clarified by Samuelson, et al (Proc. Natl. Acad. Sci. U.S., 77, 2014 (1980)), and it has been found that it is formed by metabolism from arachidonic acid by aid of 5-lipoxygenase. It has been reported that various peroxy lipids such as hydroperoxyeicosatetraenoic acid, hydroxyeicosatetraenoic acid, leucotriene B, SRS-A, etc., which are formed by metabolism by aid of lipoxygenase, are chemical mediators that contract various smooth muscles, for example, smooth muscles of respiratory system (trachea, bronchus, pulmonary tissue), vascular system, digestive organ, accelerate capillary permeability, stimulate migration of leukocytes and smooth muscles of aortic tunica media, and as the result cause bronchial asthma, allergic diseases (atopic dermatitis, inflammation of organs, etc.), diseases of circulatory organs (edema, ischemic heart disease, hypertension, ischemic brain disturbance, arteriosclerosis, etc.) or cause inflammatory diseases. However, no effective compounds for diseases due to lipoxygenase metabolic products have been developed.

As a result of searching for preventive and healing agents for diseases due to lipoxygenase metabolic products, it has been found that compounds represented by the formula (I) can inhibit lipoxygenase very strongly and suppress production and release of its metabolic products remarkably and, thus, are useful as a preventive and healing agent for diseases due to lipoxygenase metabolic products.

The alkyl group represented by R in formula (I) can be straight or branched and includes methyl, ethyl, n-propyl, i-propyl, n-butyl, i-butyl, n-pentyl, n-hexyl, n-heptyl, n-octyl, 2-ethylhexyl, n-nonyl, n-decyl, n-undecyl, n-dodecyl, n-tridecyl, n-tetradecyl, n-pentadecyl, etc.

Compounds (I) can be synthesized, as given below, according to, for example, J. W. Cornforth, et al, procedure (Biochem. J. 63, 124 (1956)):

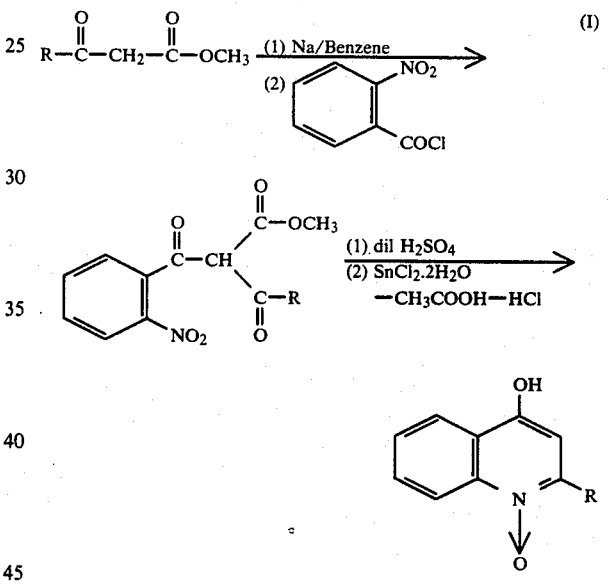

wherein R is an alkyl group having 1–15 carbon atoms.

Compounds of formula (I) wherein the R group has 7, 8, 9, and 11 carbon atoms can be produced by culturing a strain belonging to the genus Pseudomonas, followed by purification and isolation according to J. W. Lightbrown procedure (J. Gen. Microbiol. 11 477–492 (1954)).

Compounds (I) inhibit the lipoxygenase activity strongly. Especially, compound (I) whose R is an alkyl group having 3–15, above all, 5–15 carbon atoms have very strong inhibiting action upon lipoxygenase. Compounds (I) are useful for healing and preventing bronchial asthma, various allergic diseases (allergic rhinitis, nettle rash, etc.), ischemic heart disease, hypertension, ischemic brain disturbance, arteriosclerosis, inflammatory diseases, etc. Dosage for these purposes depends upon the desired healing effect, way of administration, healing period, age, body weight, etc., and usually is 0.1–10 mg/kg per day for an adult human as compounds (I) through oral or parenteral route (for example, injection, application, inhalation, etc.). Compounds (I) can be administered as such, but generally administered in the form of tablets, pills, powder, granules, capsules, suppository injection, etc. Conventional pharmaceutically acceptable carriers can be used for medical compositions of this invention and include lactose, dextrose, sucrose, sorbitol, mannitol, glucose, cellulose, cyclodextrin, talc, starch, methylcellulose, gelatin, arabic gum, polyethylene glycol, carboxymethylcellulose, hydroxypropylcellulose, sodium benzoate, sodium hydrogen sulfite, aluminium stearate, magnesium stearate, mineral oil, vegetable oil, white vaseline, liquid paraffin, etc., and can be appropriately selected in view of the kind of preparations. The present composition can contain 0.01–85 weight percent of compound (I).

TEST EXAMPLE 1

Figure 1:
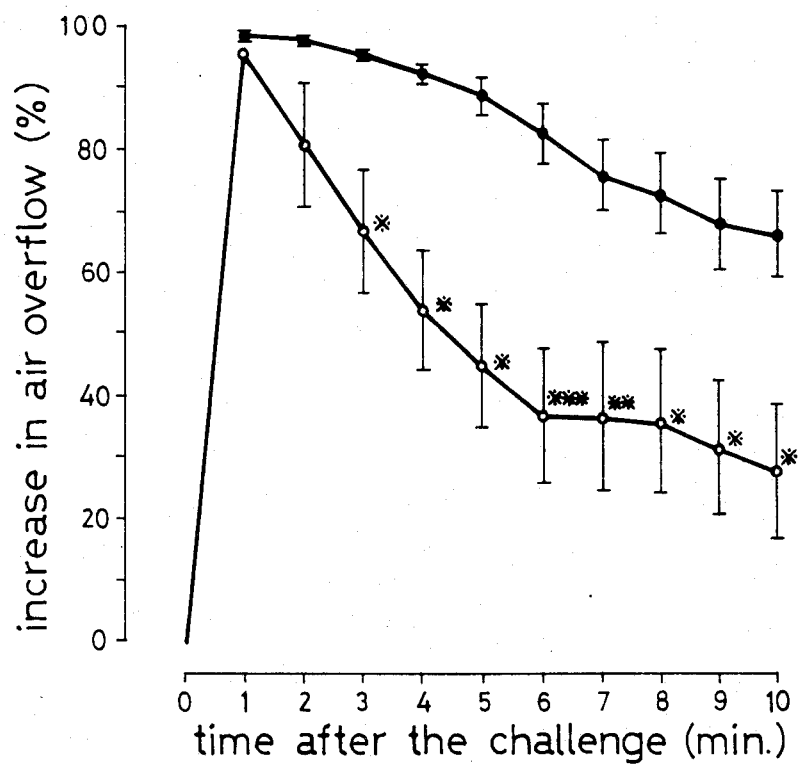
FIG. 1 of the accompanying drawings shows a relationship between an increase in air volume flowing from the cannule side way and a time after antigen, egg white albumin (EWA) is administered to passively sensitized guinea pigs, wherein -o- shows the case of administering the effective compound and -o- the case of the control.

An inhibiting action of 2-n-heptyl-4-hydroxyquinoline-N-oxide upon lipoxygenase was determined by in vitro test according to the following procesure:

(a) Procedure for determining the inhibiting action upon blood platelet 12-lipoxygenase:

Determination was carried out according to D. H. Nugtern, et al, procedure (Biochem. Biophys. Acta, 380, 299 (1975)). That is, a preparation prepared from bovine blood platelets was used as an enzyme source. The blood platelet lipoxygenase preparation and 2-n-heptyl-4-hydroxyguinoline-N-oxide were brought into contact with each other in a 0.01M tris hydrochloric acid buffer solution (pH 7.4) at 30° C. for 5 minutes in advance, and then 35 $\mu$M of [$^{14}$C]arachidonic acid was added thereto. The mixture was incubated at 30° C. for 10 minutes. The reaction product was extracted with ethyl acetate/methanol/0.2M citric acid (30/4/1), and then separated by thin layer chromatography (developing solvent system: ligroin/ethyl ether/acetic acid: (50/50/1). The spot of 12-hydroxy-5,8,10,14-eicosatetraenoic acid in the product was scraped off and $^{14}$C was measured by a liquid scintillation counter.

(b) Procedure for determining the inhibiting action upon leukocyte 5-lipoxygenase:

Determination was carried out according to modified B. A. Jakschik, et al, procedure (Biochem. Biophys. Res. Commun. 95, 103 (1980)). That is, leukemic basophilic granulocyte cells of rats (RBL-1, ATCC No. CRL 1378) were used as a 5-lipoxygenase enzyme source. The cells and 2-n-heptyl-4-hydroxyquinoline-N-oxide were brought into contact with each other in a 0.07 M tris hydrochloric acid buffer solution in the presence of 0.7 mM calcium chloride at 37° C. for 5 minutes, and then 20 $\mu$M of [$^{14}$C]-arachidonic acid was added thereto. The mixture was incubated at 37° C. for 5 minutes. The reaction product was extracted with ethyl acetate/methanol/0.2M citric acid (30/4/1), and then separated by thin layer chromatography (developing solvent: petroleum ether/ethyl ether/acetic acid: 50/50/1). Spots of 5-hydroxy-5,8,10,14-eicosatetraenoic acid in the product were scraped off and $^{14}$C was measured by a liquid scintillation counter.

As is apparent from the results shown in Table 1, the present compound has an inhibiting action upon both enzymes; i.e., 12-lipoxygenase and 5-lipoxygenase at a low concentration. When the intensity was compared with that of known compound BW-755C, i.e., 3-amino-1-(3-trifluoromethylphenyl)-2-pyrazoline hydrochloride, it was found that the inhibiting action upon 12-lipoxygenase was almost equal to that of known compound, but the inhibiting action upon 5-lipoxygenase was much better in the present compound.

TABLE 1

| Compounds | Inhibiting action upon 12-lipoxygenase and 5-lipoxygenase $IC_{50}^{(1)}$, $\mu$M | |
|---|---|---|
| | 12-lipoxygenase | 5-lipoxygenase |
| 2-n-heptyl-4-hydroxy-quinoline-N—oxide | 30 | 0.15 |
| BW-755C | 25 | 4.0 |

$^{(1)}$Concentration of the compound required for 50% inhibition of enzyme activity

TEST EXAMPLE 2

Inhibiting actions of compounds in Table 2 upon lipoxygenase were determined in the same manner as in Test Example 1. The results are shown in Table 2, from which it is apparent that these compounds exhibit specific and strong inhibiting actions especially upon 5-lipoxygenase.

TABLE 2

| Compound | Inhibiting action upon 12-lipoxygenase and 5-lipoxygenase | |
|---|---|---|
| | 12-lipoxygenase$^{(1)}$ | 5-lipoxygenase$^{(2)}$ |
| 2-n-propyl-4-hydroxy-quinoline-N—oxide | 46.3% | 110.0 $\mu$M |
| 2-n-undecyl-4-hydroxy-quinoline-N—oxide | 55.7% | 0.2 $\mu$M |
| 2-n-pentadecyl-4-hydroxy-quinoline-N—oxide | 56.0% | 1.0 $\mu$M |

$^{(1)}$inhibiting ratio with 1,000 $\mu$M of each compound
$^{(2)}$concentration of each compound required for 50% inhibition of enzyme activity

TEST EXAMPLE 3

An inhibiting action of 2-n-heptyl-4-hydroxyquinoline-N-oxide upon SRS-A production was determined according to the following procedure:

Procedure:

According to Watanabe-Kohno and Parker procedure (J. Immunol., 125, 946 (1980)), 20 mg of egg white albumin (hereinafter abbreviated as EWA), was dissolved in 10 ml of physiological saline solution, and the resulting solution was added to an equal volume of Freund's complete adjuvant to prepare an emulsion. Then, 1 ml of the emulsion was administered subcutaneously in the plantar surface of the hind paws of guinea pigs to make the animals actively sensitized. Three to five weeks thereafter, the guinea pigs were sacrificed by exsanguination from the carotid artery, and the Tyrode's solution was perfused through right cardiac ventricle to wash lungs and remove blood. Then, the lungs were isolated and cut to pieces of about 2 mm size in the chilled Tyrode's solution with scissors, filtered through 2 sheets of gauze. Then, 400 mg of the fragments were distributed into individual test tubes containing 5 ml of the Tyrode's solution. The lung pieces were preincubated at 37° C. for 10 minutes, 0.5 ml of a test solution at various concentrations was added thereto, and the incubation was continued for 10 minutes at 37° C. Then, 0.5 ml of EWA (20 mg/ml) was added thereto, and the mixture was further incubated for 15 minutes. The reaction was discontinued by ice-cooling the mixture, and then the mixture was filtered through a sheet of gauze.

The amount of SRS-A in the filtrate was bioassayed using guinea pig ileum according to the Magnus procedure. That is, the ileums were suspended in 10 ml of organ bath filled with the Tyrode's solution (31 ±1° C., aerated with 95% $O_2$+5% $CO_2$ gas mixture), and their movements were recorded on a recorder with a pen (Hitachi: QPD54) through an isotonic transducer (Nihon Koden: JD112S). After the ileum contraction reaction by $10^{-7}$ M histamine was stabilized, 1 ml of the filtrate was added to the organ bath in the presence of 5 x $10^{-7}$ M atropine and $10^{-6}$ M tripelennamine to cause the ileum contraction reaction. It was known that the ileum contraction reaction by SRS-A was increased by repetitive applications and, therefore, after the reaction by at least 5 applications of the SRS-A prepared in advance became constant, control filtrate and a filtrate containing a test solution were used. The reaction was almost completely suppressed by $3\times10^{-7}$ M of FPL-55712, a specific antagonist of SRS-A. The amount of SRS-A contained in the individual filtrates was given in percentage, where the amount of control SRS-A was designated as 100%.

Test results:

As shown in Table 3, the formation of SRS-A was suppressed by application of 4, 40, and 400 µg/ml of the present compound in a dose dependent manner. Furthermore, its intensity was obviously better than the suppressing action of BW-755C measured at the same time.

TABLE 3

| Suppressing action upon production of SRS-A | | |
|---|---|---|
| Compound | Concentration µg/ml | Suppressing Ratio % |
| 2-n-heptyl-4-hydroxyquinoline-N—oxide | 4 | 26.2 ± 4.2 |
|  | 40 | 60.1 ± 3.7 |
|  | 400 | 84.3 ± 1.1 |
| BW-755C | 40 | 23.8 ± 8.8 |

TEST EXAMPLE 4

Suppressing actions of 2-n-propyl-4-hydroxyquinoline-N-oxide and 2-n-undecyl-4-hydroxyquinoline-N-oxide upon production of SRS-A were determined in the same manner as in Test Example 3. The results are shown in Table 4, from which it is apparent that both compounds suppress the production of SRS-A.

TABLE 4

| Suppressing action upon production of SRS-A | | |
|---|---|---|
| Compound | Concentration µg/ml | Suppressing ratio % |
| 2-n-propyl-4-hydroxy-quinoline-N—oxide | 8.3 | 34.1 |
| 2-n-undecyl-4-hydroxy-quinoline-N—oxide | 8.3 | 17.5 |

TEST EXAMPLE 5

Suppressing action of 2-n-heptyl-4-hydroxyquinoline-N-oxide upon the airway contraction reaction of passively sensitized guinea pigs was determined according to the following procedure:

Procedure:

Anaphylactic airway contraction reaction of passively sensitized guinea pigs by antigen administration was determined according to modified Konzett and Rössler procedure (Arch. exp. Path. Pharmakol., 195, 71 (1940)). Anti-EWA guinea pig serum (1 ml/animal) was intraperitoneally administered into normal guinea pigs to make the animals passively sensitized, and 24 hours thereafter, a tracheal cannule was inserted and fixed to the guinea pig under urethane anesthesia. An artificial respirator and a bronchospasm transducer were connected to the cannule. After the spontaneous respiration was stopped by intravenous injection of 10 mg/kg of gallamine triethiodide, 1 mg/kg of EWA was injected into the jugular vein to cause anaphylactic airway contraction, and the volume of air overflow from the tracheal cannule sideway was recorded on a polygraph through the transducer. After the end of measurement, the trachea was completely blockaded. The state of complete blockade was regarded as a maximum contraction, and the results were given in percentage to the maximum contraction.

Test results:

Relationship between an increase in air overflow when antigen EWA was administered to passively sensitized guinea pig (percentage to the air overflow at the maximum contraction) and time (minutes) after the challenge is shown in the graph in the accompanying drawings, wherein -o-, shows the case of administering 10 mg/kg of 2-n-heptyl-4-hydroxyquinoline-N-oxide (P.O.) one hour before the antigen administration (6 guinea pigs) and -o- shows the case of control (18 guinea pigs), and *,  and * show risks of not more than 5%, not more than 1% and not more than 0.1%, respectively.

As is apparent from the graph, the reaction was significantly suppressed when the N-oxide of the present invention was administered in advance.

Procedures for preparing the composition of this invention are shown in the following examples:

EXAMPLE 1

Tablets

A 10% hydroxypropylcellulose solution is added to a mixture consisting of 100 g of 2-n-heptyl-4-hydroxyquinoline-N-oxide, 40 g of lactose, 18 g of corn starch and 10 g of carboxymethylcellulose calcium, and the mixture is kneaded. The mixture is then granulated by an extrusion granulator with 1.0 mm basket, and the granules are dried at 60° C. The dried granules are screened on a 16-mesh sieve, and magnesium stearate is added to the screened granules to prepare tabletting granules. According to the ordinary procedure, tablets, 8 mm in size, each containing 100 mg of the N-oxide in one tablet (170 mg), are prepared.

EXAMPLE 2

Capsules

A 10% hydroxypropylcellulose solution is added to a mixture consisting of 50 g of 2-n-undexyl-4-hydroxyquinoline-N-oxide, 80 g of lactose and 38 g of potato starch, and the mixture is kneaded. The mixture is granulated in the same manner as in Example 1, and after addition of magnesium stearate, capsules each containing 50 mg of the N-oxide in one capsule (170 mg) are prepared according to an ordinary procedure.

EXAMPLE 3

Soft Capsules

At first, 10 g of 2-n-heptyl-4-hydroxyquinoline-N-oxide is dissolved in 100 g of soybean oil, and the solution is filled into capsules, each containing 10 mg of the N-oxide, according to the ordinary procedure, to prepare soft capsules.

EXAMPLE 4

Ointment

At first, 20 g of 2-n-heptyl-4-hydroxyquinoline-N-oxide is mixed with a mixture of white vaseline and liquid paraffin to prepare an ointment containing 100 mg/g of the N-oxide.

What is claimed is:

1. A composition in the form of tablets, pills, powder, granules, capsules or suppositories for treating diseases due to lipoxygenase metabolic products, which comprises an effective lipoxygenase inhibiting amount of a compound represented by the formula:

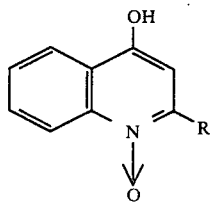

wherein R is an alkyl group having 1 to 15 carbon atoms and at least one pharmaceutically acceptable carrier.

2. A composition according to claim 1, wherein R in the formula is an alkyl group having 3 to 15 carbon atoms.

3. A composition according to claim 2, wherein R in the formula is an alkyl group having 5 to 15 carbon atoms.

4. A method for treating diseases due to lipoxygenase metabolic products, which comprises administering to a human an effective amount of a composition consisting essentially of a compound represented by the formula:

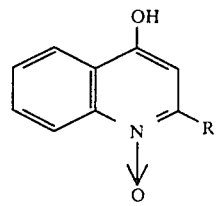

wherein R is an alkyl group having 1 to 15 carbon atoms and at least one pharmaceutically acceptable carrier.

5. A method according to claim 4, wherein R in the formula is an alkyl group having 3 to 15 carbon atoms.

6. A method according to claim 5, wherein R in the formula is an alkyl group having 5 to 15 carbon atoms.

7. A method according to claim 4, wherein the effective amount is 0.1 to 10 mg/kg/day of said compound.

8. A method according to claim 5, wherein the effective amount is 0.1 to 10 mg/kg/day of said compound.

9. A method according to claim 6, wherein the effective amount is 0.1 to 10 mg/kg/day of said compound.

* * * * *